United States Patent [19]

Fex et al.

[11] 4,177,269

[45] Dec. 4, 1979

[54] NOVEL 17-ESTERS OF 17α-HYDROXY GESTOGENS, COMPOSITIONS CONTAINING SUCH COMPOUNDS, PROCESSES FOR THEIR PREPARATION AND METHODS OF TREATMENT THEREWITH

[75] Inventors: Hans Fex; Bertil Hansen, both of Helsingborg; Krister Holmberg, Angelholm; Bertil Högberg; Imre Könyves, both of Helsingborg, all of Sweden

[73] Assignee: Aktiebolaget Leo, Sweden

[21] Appl. No.: 760,152

[22] Filed: Jan. 17, 1977

[30] Foreign Application Priority Data

Jan. 22, 1976 [GB] United Kingdom ............... 02419/76

[51] Int. Cl.$^2$ ............................................. A61K 31/56
[52] U.S. Cl. ................................. 424/243; 260/397.4; 260/349; 260/239.5
[58] Field of Search ...................... 260/397.4; 424/243

[56] References Cited

U.S. PATENT DOCUMENTS

| 2,753,360 | 7/1956 | Kaspar et al. ..................... 260/397.4 |
| 4,029,778 | 6/1977 | Fex et al. ............................. 424/243 |

OTHER PUBLICATIONS

JACS (1959), vol. 81, pp. 2712 and 3485.
Everett et al., J. Chem. Soc., pp. 2386–2392, (1953).

*Primary Examiner*—Elbert L. Roberts
*Attorney, Agent, or Firm*—Gordon W. Hueschen

[57] ABSTRACT

This invention relates to novel 17α-esters of gestogens having an antitumour activity and to the preparation thereof. The invention is also concerned with pharmaceutical compositions containing the said compounds, and method of treatment therewith.

18 Claims, No Drawings

NOVEL 17-ESTERS OF 17α-HYDROXY GESTOGENS, COMPOSITIONS CONTAINING SUCH COMPOUNDS, PROCESSES FOR THEIR PREPARATION AND METHODS OF TREATMENT THEREWITH

This invention relates to novel 17α-esters of gestogens having an antitumour activity, and to the preparation thereof. The invention is also concerned with pharmaceutical compositions containing the said compounds, and methods of treatment therewith.

BACKGROUND OF THE INVENTION

It is known that esters of certain steroids with alkanoic acids containing a phenyl group substituted with a bis(2-chloroethyl)amino group have antitumour activities in animals and human beings. The acid part of such known esters has in the main been 4-/N,N-bis(2-chloroethyl)amino/phenylacetic acid and 4-/4-(N,N-bis(2-chloroethyl)amino)phenyl/butanoic acid.

The types of steroids which have been investigated are estrogens, androgens, corticoids, and one sterol, cholesterol. The hydroxy group or groups in these steroids which have been esterified have been situated in one or two of the positions 3-(estrogens), 3β-(androgens, pregnenolone, and cholesterol), 17β-(estrogens and androgens) and 21-(corticosteroids).

Such esters are described in e.g. J. Med. Chem. 11 (1968) 1106, ibid 12 (1969) 810, ibid 15 (1972) 1158, and U.S. Pat. No. 3,732,260.

No esters of gestogens are known which in their acid part contain an alkylating group such as the bis(2-chloroethyl)amino group, although numerous gestogens are known which contain esterifiable hydroxy groups in various positions of the steroid molecules, e.g., at the 3, 11, 16, and 17-positions, much less are any such gestogen esters known in which the esterification is at the position of particular interest to the present invention, namely in the 17α-position.

It has now, surprisingly, been found that the esters of the present invention being 17α-esters of gestogens are active against animal tumours, and that they also show a very low toxicity resulting in very favourable therapeutic indexes.

The esters of this invention are of value in the treatment of tumours, for instance, in uro-genital organs, such as the ovaries, the endometrium, the prostate, the bladder, and the kidneys. The compounds are particularly useful in the treatment of tumours situated in organs which are targets for gestogens, such as the endometrium and the mammary glands. The compounds of the invention are also valuable in the treatment of haematological disorders.

SUMMARY OF THE INVENTION

The new 17α-esters of gestogens of the invention correspond to the general formula I as defined below.

The compounds of the invention have shown effect in inhibiting the growth of tumours, e.g. Ehrlich ascites, Melanoma Harding-Passey, Hepatoma AH 130, Lymphocytic leukemia (L 1210), and Walker carcinoma 256, according to the procedures set by Cancer Chemotherapy National Service Center (see: Cancer Chemotherapy Reports, January 1959 and December 1962).

The compounds of the invention have also been found to possess a high affinity to specific gestogen binders, i.e. receptors, in the cell cytoplasm.

The compounds of the invention can be employed in disorders responsive to treatment with antitumour agents and with immunosuppressive agents, as such or combined with either solid or liquid carriers or diluents and made available in varying amounts in such pharmaceutical forms, as, e.g., tablets, pills, capsules, pellets, powders, ointments, suppositories, aqueous or non-aqueous suspensions, and non-aqueous solutions.

Accordingly, one object of the invention is to provide new compounds, having the general formula I, having the aforesaid activity, preferably also with a relatively low degree of toxicity.

A second object is to provide such type of compounds, which can be employed in disorders responsive to treatment with anti-tumour agents and with immunosuppressive agents, for the amelioration or palliation thereof.

A further object of the invention is to provide a method of treating a living animal body suffering from disorders responsive to treatment with anti-tumour agents and with immunosuppressive agents, for the amelioration or palliation thereof, which comprises the step of administering to said living animal body a compound having the general formula I, said compound being administered in an amount sufficient to at least mitigate said disorders.

Yet another object of the invention is to provide compositions containing as an active ingredient one or more of the compounds, having the general formula I, preferably together with a pharmaceutically acceptable carrier and, if desired, other pharmacologically acitve agents.

Accordingly what we believe and claim to be our invention comprises novel compounds having the general formula:

$$\text{St—R} \qquad \qquad \text{I}$$

wherein R is

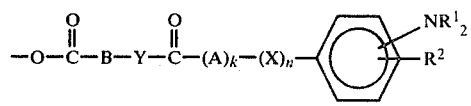

where $R^1$ is a β- or γ-halogensubstituted alkyl group having 2 to 4 carbon atoms, the halogen being chlorine or bromine; where $R^2$ is selected from the group consisting of hydrogen, lower alkyl, lower alkoxy, and halogen;

where A is a straight hydrocarbon chain having at most 4 carbon atoms and being saturated or containing one double bond. At most 2 hydrogen atoms of A may be replaced by lower alkyl and at most one of the hydrogen atoms situated at the carbon atom adjacent to a

group may be replaced by a group selected from the group consisting of amino and lower alkanoylamino;

where B is a straight saturated hydrocarbon chain having at most 4 carbon atoms. At most 2 hydrogen atoms of B may be replaced by lower alkyl;

where X and Y are independently selected from the group consisting of —O—, —NH—, and —S—;

where k, and n are independently selected from the group consisting of zero and one; n always being zero when k is zero;

wherein St is a residue of a steroid having a cyclopentanophenanthrene carbon-carbon skeleton containing up to a maximum of 40 carbon atoms, inclusive of substituents, said carbon-carbon skeleton including a carbon-carbon skeleton of a steroid nucleus selected from the group consisting of pregnane and 19-norpregnane nuclei, having from zero up to a maximum of 4 double bonds, said steroid residue being attached in its 17-position to R, said position being identified according to steroid nomenclature.

This invention also comprises novel compounds being useful as intermediates for preparing the antitumour compounds I and having the general formula:

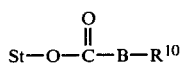      XV wherein St and B have the meaning given above, and where St is attached in its 17-position to the group

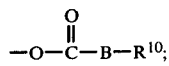

wherein $R^{10}$ is selected from the group consisting of hydroxy, mercapto, hydroxy and mercapto esterified with a carboxylic acid or a sulfonic acid having at most 15 carbon atoms, amino, acylamino having at most 15 carbon atoms, and azido. When $R^{10}$ is amino, those heterocyclic compounds are included which are formed by cyclisation reaction of said group and the keto group in the 20-position of the steroid molecule.

In this disclosure the expression "lower" means that the group referred to contains one to four carbon atoms, inclusive. Thus, lower alkyl, lower alkoxy, and lower alkanoyl include: methyl, ethyl, propyl, iso-propyl, butyl, secondary butyl, iso-butyl, tertiary butyl, methoxy, ethoxy, propoxy, isopropoxy, butoxy, isobutoxy, secondary butoxy, tertiary butoxy, acetyl, propionyl, butyryl, and isobutyryl.

The nomenclature used in this disclosure is in accordance with the I.U.P.A.C. 1957 Rules for Nomenclature of Steroids. Whenever used herein the general formula I and XV and the symbols A, B, X, Y, $R^1$, $R^2$, $R^{10}$, St, k, m, and n have the meaning given above.

Among those compounds covered by the above general formula I those are preferred wherein the halogen atom of $R^1$ is in $\beta$-position and the alkyl group of $R^1$ is ethyl, n-propyl, or n-butyl.

Compounds, wherein $R^1$ is $-CH_2-CH_2-Cl$ are particularly preferred.

The group $-NR_2^1$ is preferably in m- or p-position, particularly when k and n are zero and in p-position when at least one of k and n is one.

It is preferred that $R^2$ is hydrogen or lower alkyl.

When the group $-NR_2^1$ is in m-position, it is preferred that $R^2$ is in p-position and different from hydrogen, especially when k and n are zero.

When A is substituted with an amino or a lower alkanoylamino group, it is preferred that n is zero and that A is a saturated hydrocarbon chain containing 2 carbon atoms.

It is preferred that n is zero.

X, when present, is preferably $-O-$ or $-NH-$, and especially $-O-$, when k is one.

When n is one and k is zero, compounds with highly active metabolites are obtained.

It is preferred that Y is $-O-$ or $-NH-$.

When k is one, it is particularly preferred that Y is $-O-$.

Among those compounds covered by the above general formula XV those are preferred as intermediates wherein $R^{10}$ is hydroxy, hydroxy esterified with a carboxylic acid having at most 10 carbon atoms, amino, and azido.

The residue of a steroid, St, as defined above, has a carbon-carbon skeleton preferably selected from the group consisting of: the carbon-carbon skeleton of pregn-4-ene, pregna-4,6-diene, and of 19-norpregn-4-ene.

Preferred nuclei of said steroid residue having the aforementioned skeletons are as follows: 17α-pregn-4-ene-3,20-dione, 17α-pregna-4,6-diene-3,20-dione, and 17α-(19-norpregn-4-ene-3,20-dione) nuclei, having the radical, R, attached to the said 17-position.

Preferably, any further substitution that is present in the carbon-carbon skeletons of said steroid nuclei, being at most a tetrasubstitution wherein the positions of the steroid carbon-carbon skeleton which are substituted are selected from the positions consisting of the 1-, 2-, 6-, and 16-positions, comprises at least one substituent preferably selected from the group consisting of methyl, methylene, fluoro, and chloro. It is particularly preferred that said substitution is at most a disubstitution, comprising one or two substituents selected from the group consisting of 6-methyl, 6-chloro, 6-fluoro, 1,2-methylene, and 16-methylene.

The steroid residue (St) is preferably derived from following steroids:
17α-hydroxypregn-4-ene-3,20-dione (17α-hydroxyprogesterone),
17α-hydroxy-19-norpregn-4-ene-3,20-dione,
6α-fluoro-17α-hydroxypregn-4-ene-3,20-dione,
6α-chloro-17α-hydroxypregn-4-ene-3,20-dione,
17α-hydroxy-6α-methylpregn-4-ene-3,20-dione (medroxyprogesterone),
17α-hydroxy-6α,16α-dimethylpregn-4-ene-3,20-dione,
17α-hydroxypregna-4,6-diene-3,20-dione,
6-fluoro-17α-hydroxypregna-4,6-diene-3,20-dione,
6-chloro-17α-hydroxypregna-4,6-diene-3,20-dione (chlormadinone),
17α-hydroxy-6-methylpregna-4,6-diene-3,20-dione (megestrol),
6-chloro-17α-hydroxy-1α,2α-methylenepregna-4,6-diene-3,20-dione (cyproterone),
6-chloro-17α-hydroxy-16α-methylpregna-4,6-diene-3,20-dione,
6-chloro-17α-hydroxy-16-methylenepregna-4,6-diene-3,20-dione,
17α-hydroxy-6,16α-dimethylpregna-4,6-diene-3,20-dione,
6-fluoro-17α-hydroxy-16-methylene-9β,10α-pregna-4,6-diene-3,20-dione,
6-fluoro-17α-hydroxy-1β,2β-methylene-9β,10α-pregna-4,6-diene-3,20-dione.

Among the steroids mentioned above 17α-hydroxyprogesterone, medroxyprogesterone, chlormadinone, cyproterone, and megestrol are particularly preferred.

In the following, references to the literature are given by elevated, underlined, numbers, e.g. "this method[18]

is". The numbers refer to literature sources listed after the examples.

METHODS OF PREPARATION

The compounds having structures I and XV may be prepared by conventional methods.

A general process (method 1 below) for preparing compounds having structure I is as follows:

METHOD 1

Compound I is prepared by reacting a 17-hydroxysteroid having structure III, or a reactive derivative thereof, and an acid IV, or a reactive derivative thereof. (See for instance references 1 and 2 for the esterification of 17-hydroxysteroids.)

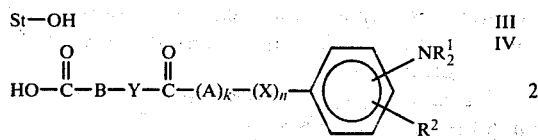

Among other methods for preparing compounds having structure I the following may be mentioned.

METHOD 2

Reacting a 17-hydroxyester of a steroid having structure II and an acid V, or a reactive derivative thereof, provides compound I.

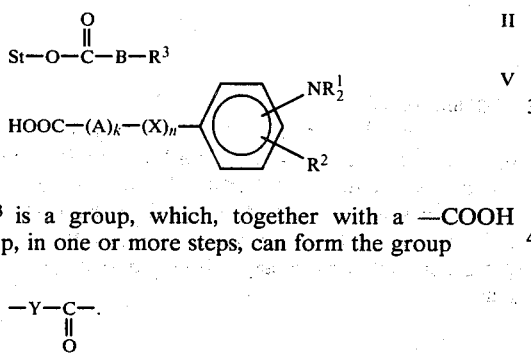

$R^3$ is a group, which, together with a —COOH group, in one or more steps, can form the group $$-Y-\overset{\text{O}}{\underset{\|}{C}}-.$$

METHOD 3

Reacting a halide VI and a compound VII, or a reactive derivative thereof, produces compound I, wherein n is one.

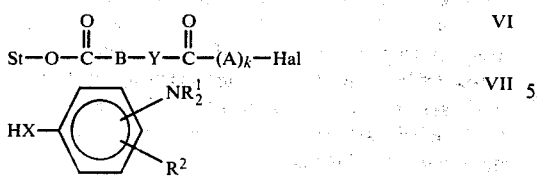

Whenever used herein Hal means a halogen atom selected from chlorine and bromine.

METHOD 4

A 17-hydroxysteroid having structure III and having one hydrogen atom in 21-position replaced by a hydroxyl group and a suitable derivative of acid IV are reacted to form a 17,21-ortho ester. (See reference 3 for the preparation of ortho esters.)

The 17,21-ortho ester is then by known methods converted into compound I. (See reference 4 for the transformation of 17,21-ortho esters into 17-monoesters.)

A general process for preparing compounds having structure XV is as follows:

METHOD 5

Reaction of compound III, or a reactive derivative thereof, and an acid XVI, or a reactive derivative thereof, produces compound XV or a compound which, in one or more steps, can be transformed into said compound.

$$\text{HOOC}-\text{B}-\text{R}^{11} \qquad \text{XVI}$$

$R^{11}$ is the group $R^{10}$ or a group, such as a halogen, which, in one or more steps, can be transformed into $R^{10}$.

In synthetizing compounds having structures I and XV by any of the methods mentioned above each group of the starting materials involved must be compatible with the process in question or, if necessary, protected during one or more reaction steps and then converted to the desired group.[5,6] Pertinent examples of groups that may be protected are the carbonyl groups in the steroid and an amino group of A.

Examples of protective groups for carbonyl groups in the steroids are ketals, e.g. 1,3-dioxolans, hemithioketals, e.g. 1,3-oxathiolans, and dithioketals, e.g. 1,3-dithiolans. 1,3-Dioxlan derivatives may be prepared by treatment of carbonyl compounds with ethylene glycol in the presence of an acid catalyst,[19] and the carbonyl groups may be regenerated upon treatment with acids, such as hydrochloric acid in acetone.[20] 1,3-Oxathiolans may be formed by acid-catalyzed reaction between 2-mercaptoethanol and carbonyl compounds[21] and they may be reconverted into ketones by treatment with acids, such as hydrochloric acid in dioxan,[22] or by the action of Raney nickel.[20] 1,3-Dithiolans may be prepared by acid-catalyzed reaction of carbonyl compounds with ethanedithiol,[21] and the carbonyl functions may subsequently be regenerated by the action of mercuric salts.[23]

Examples of protective groups for an amino group of A are substituted or unsubstituted benzyloxycarbonyl and benzyl groups. Such N-benzyloxycarbonyl derivatives may be prepared by reaction of amino compounds with benzyl chloroformate in the presence of an alkaline catalyst,[24] and the amino group may subsequently be regenerated by treatment with acidic reagents, such as hydrogen chloride[25] or by catalytic hydrogenation.[26] Mono-N-benzyl derivatives may be synthesized by treatment of amines with benzyl chloride in the presence of base and subsequent partial hydrogenation of the dibenzyl compounds formed;[27] debenzylation may be achieved by catalytic hydrogenation.

It is understood that one or more of the steps described in the methods 1-4 above may be carried out with one or both of the halogen atoms of $R^1$ replaced by groups, e.g. hydroxyl or sulfonic esters thereof, which subsequently can be substituted by Hal, thus providing the desired compound.

Methods 1-5 above are illustrated by the following processes (a-e):

(a) A process according to method 1, characterized by reacting, in one or more steps, compound III, or a reactive derivative thereof, and acid IV, or a reactive derivative thereof, preferably in the presence of an anhydride or a catalyst.

Examples of reactive derivatives of acid IV are its anhydride or acyl halide, e.g. acyl chloride. A suitable anhydride is trifluoroacetic anhydride, and suitable catalysts are, for instance, strong organic or inorganic acids, such as arylsulfonic acids or perchloric acid.

Acid IV may be prepared by reacting acid V, or a reactive derivative thereof, and a compound VIII, wherein $R^4$ is a suitable carboxyl protecting group,[15] e.g. a benzyl group, and subsequent removal of the protective group by a suitable method,[15] e.g. catalytic hydrogenation.

$$R^4-O-\overset{O}{\underset{\|}{C}}-B-R^3 +$$

VIII

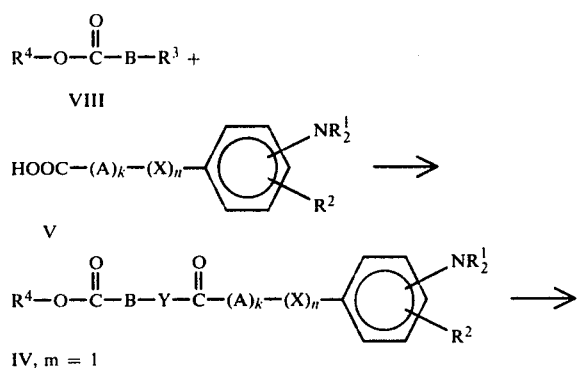

IV, m = 1

When the group

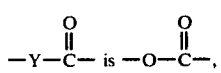

the group $R^3$ may be a halogen atom, a hydroxyl group, or a reactive organic ester thereof. If $R^3$ is a halogen atom, acid V is suitable either in the form of an ion pair, e.g., by using an equivalent or a catalytic amount of a quaternary ammonium cation as counter-ion,[7] or in the form of a metal salt, e.g., of an alkali metal or silver.[8] If $R^3$ is a hydroxyl group, acid V is either free or in the form of its anhydride or acyl halide, e.g., acyl chloride, and the reaction is preferably performed in the presence of a carbodiimide, such as dicyclohexylcarbodiimide, an anhydride, such as trifluoroacetic anhydride, or a catalyst, e.g., a strong organic or inorganic acid, such as an arylsulfonic acid or perchloric acid, or a base, such as pyridine, N,N-dimethylaniline, or triethylamine.[9] If $R^3$ is hydroxyl esterified with an organic acid, e.g., a sulfonic acid, such as 4-toluenesulfonic acid, or a lower alkanoic acid, optionally substituted with a member of the group consisting of chlorine and fluorine, such as trifluoroacetic acid, acid V is suitably either free or in the form of an ion pair, e.g., with a quaternary ammonium ion as counter-ion, and the reaction may be performed in the presence of a catalyst, e.g. a strong acid, such as sulfuric acid or 4-toluenesulfonic acid, a base, such as an aluminium alkoxide, or a quaternary ammonium salt, such as tetrabutylammonium salt.[28]

When the group

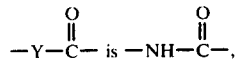

the group $R^3$ may be an amino group. Acid V is suitably in the form of its anhydride, mixed anhydride, ester with lower alkanols or alkenols, or acyl halide, e.g. acyl chloride. The reaction may be performed with or without a basic catalyst such as pyridine, N,N-dimethylaniline, or triethylamine.[11]

When the group

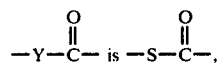

the group $R^3$ may be a hydrogen sulfide group. Acid V is either free or in the form of its anhydride, mixed anhydride, or acyl halide, e.g. acyl chloride. The reaction may be performed with or without a catalyst such as a strong acid, e.g., 4-toluenesulfonic acid, or a base, e.g., pyridine.[13]

(b) A process according to method 2, characterized by reacting, in one or more steps, compound II and acid V, or a reactive derivative thereof, preferably in the presence of a catalyst.

The same principles as described in process a regarding the formation of the group

are also valid for the condensation of the groups $-R^3$ of compound II and —COOH of acid V to give the group

of compound I.

Compound II, wherein $R^3$ is —Hal, may be prepared by reacting a 17α-hydroxysteroid having structure III and a haloacid IX, or a reactive derivative thereof, in the presence of an anhydride, such as trifluoroacetic anhydride, or a catalyst, e.g., a strong organic or inorganic acid, such as an arylsulfonic acid or perchloric acid.[1,2]

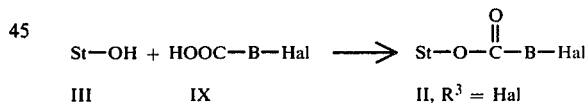

III          IX             II, $R^3$ = Hal

Compound II, wherein $R^3$ is —OH, may be prepared from the corresponding halogen compound (II, $R^3$=Hal) by known methods, for instance as described in reference 10 or in the following way: The above halogen compound is reacted with a suitable acid, such as 4-nitrobenzoic acid, in the form of its ion pair[7] or metal salt[8], to form a compound X having a labile ester bond, which is then hydrolyzed with a suitable base, e.g. potassium t-butoxide.

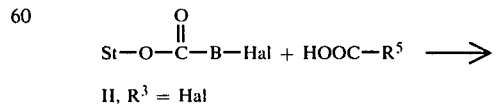

II, $R^3$ = Hal

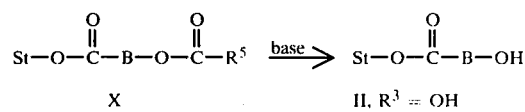

X                    II, $R^3$ = OH

R⁵ means a group, such as 4-nitrophenyl, which renders the adjacent ester bond of compound X labile.

Compound II, wherein R³ is —NH₂, may be prepared by converting the corresponding halogen compound (II, R³=Hal) to the corresponding azide (II, R³=N₃) by a suitable method, e.g., by reaction of the halogen compound with sodium azide,[12] and subsequent reduction of the azide to the desired amine. The reduction may be performed by reacting the azide with a suitable trivalent phosphorus compound, such as triphenylphosphine or trimethylphosphite, to give a compound XI, which, when reacted with water, provides compound II, wherein R³ is —NH₂.

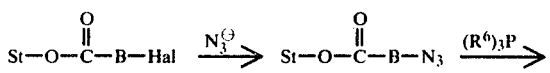

II, R³ = Hal

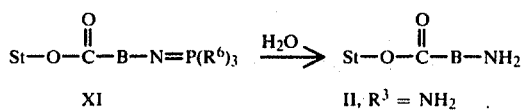

XI      II, R³ = NH₂

R⁶ means an aryl or lower alkoxy group.

Compound II, wherein R³ is —NH₂, may spontaneously undergo a cyclization, by way of reaction of the amino group with the keto group in the 20-position of the steroid, to give the cyclic amine XVIII, which may be isolated. The formation of XVIII from II, wherein R³ is —NH₂, is reversible in solution, and in the next reaction step imine XVIII is transformed into compound II, wherein R³ is —NH₂, when the latter compound is consumed by reaction with acid V.

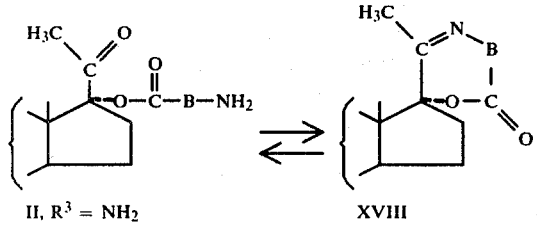

II, R³ = NH₂      XVIII

Compound II, wherein R³ is —SH, may be prepared from the corresponding halogen compound (II, R³=Hal) by known methods, e.g. by reacting the above halide with thiourea to form a compound XII, which is then hydrolyzed.[14]

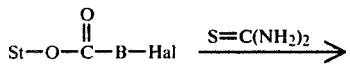

II, R³ = Hal

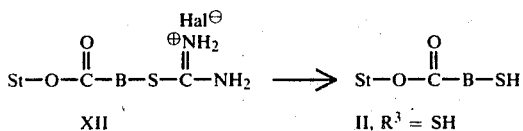

XII      II, R³ = SH (c) A process according to method 3, characterized by reacting, in one or more steps, halide VI and compound VII, or a reactive derivative hereof, with or without a catalyst.

Examples of reactive derivatices of VII, when the group —X— is —O—, are ion pairs, e.g. with a quaternary ammonium cation as counterion,[16] and metal salts of for instance silver or an alkali metal.[17] A suitable catalyst is, e.g., a quaternary ammonium salt, such as a tetrabutylammonium salt.

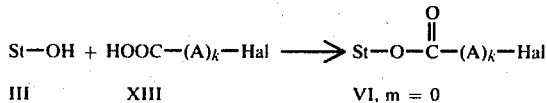

III      XIII      VI, m = 0

Halide VI, wherein m and k are one, may be prepared by known methods, e.g. by reaction of compound II, prepared as described under (b) above, and acid XIII, wherein k is one, or a reactive derivative thereof. The same principles as described under (a) regarding the formation of the group

also apply to the formation of the group

of halide VI.

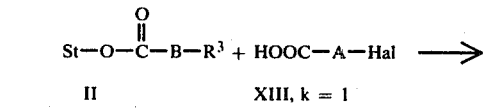

II      XIII, k = 1

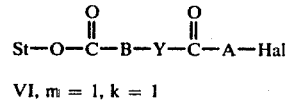

VI, m = 1, k = 1

Reacting compound II, wherein R³ is —OH, NH₂, or —SH, prepared as described under (b) above, and phosgene or its bromine analogue, provides halide VI, wherein k is zero, and Y is —O—, —NH—, and —S—, respectively.

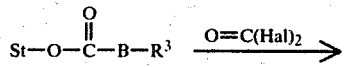

II, R³ = OH, NH₂, or SH

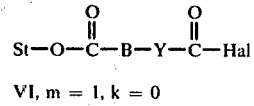

VI, m = 1, k = 0

(d) A process according to method 4, where compound III, or a reactive derivative thereof, contains a 21-hydroxyl group, characterized by reacting this 17α,21-dihydroxy compound and such a derivative of acid IV that a 17,21-ortho ester is formed,[4] the reaction preferably being performed in the presence of an acid catalyst, such as sulfuric acid. This cyclic ortho ester is then hydrolyzed, e.g., by the action of an acid, such as oxalic acid, to give the corresponding 17-acyloxy-21-hydroxy compound, which is transformed into compound I by reductive elimination of the 21-hydroxyl group, e.g. via the corresponding 21-iodo and 21-p-toluenesulfonate compounds.[4]

Acid IV may be prepared as described under (a) above. Suitable derivatives of IV are, e.g., its ortho esters with lower alkanols.[18]

(e) A process according to method 5, characterized by reacting, in one or more steps, compound III, or a reactive derivative thereof, and acid XVI, or a reactive derivative thereof, and, in those cases where $R^{11}$ is different from $R^{10}$, subsequent transformation of the product formed into compound XV. The reactions are preferably performed in the presence of an anhydride or a catalyst.

Examples of reactive derivatives of acid XVI are its anhydride and acyl halide, e.g., acyl chloride. A suitable anhydride is trifluoroacetic anhydride and suitable catalysts are, e.g., strong organic or inorganic acids, such as arylsulfonic acids or perchloric acid.

The group $R^{11}$ of acid XVI may be the group $R^{10}$ or —Hal. If $R^{11}$ is —Hal, reaction of compound III and acid XVI, or a reactive derivative thereof, produces a compound XVII which is subsequently converted to compound XV.

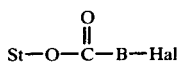

XVII

Compound XV, wherein $R^{10}$ is —OH, —SH, —N$_3$, or —NH$_2$ may be obtained from compound XVII by the methods given under (b) above for the preparation of compound II, wherein $R^3$ is —OH, —SH, —N$_3$, and —NH$_2$, respectively, from compound II, wherein $R^3$ is —Hal.

Compound XV, wherein $R^{10}$ is —OH esterified with a carboxylic or a sulfonic acid having at most 15 carbon atoms, may be prepared from compound XV, wherein $R^{10}$ is —OH, or from compound XVII by reaction with the appropriate acid, or a reactive derivative thereof. Suitable derivatives of the acid for reaction with compound XV, wherein $R^{10}$ is —OH, are its anhydride and acyl halide, e.g. acyl chloride, and the reaction is performed in the presence of an anhydride, such as trifluoroacetic anhydride, or a catalyst, e.g., a strong organic or inorganic acid, such as an arylsulfonic acid or perchloric acid, or a base, such as pyridine, N,N-dimethylaniline, or triethylamine. If the acid is reacted with compound XVII, it is suitably either in the form of an ion pair, e.g. with a quaternary ammonium cation as counterion,[7] or in the form of a metal salt, e.g. of an alkali metal or silver.[8]

Compound XV, wherein $R^{10}$ is acylamino having at most 15 carbon atoms or —SH esterified with a carboxylic acid or a sulfonic acid having at most 15 carbon atoms, may be prepared by reaction of the appropriate acid, or a reactive derivative thereof, and compound XV, wherein $R^{10}$ is —NH$_2$ and —SH, respectively. Suitable derivatives of the acid are its anhydride, mixed anhydride, or acyl halide, e.g. acyl chloride. The reaction may be performed with or without a catalyst such as a strong acid, e.g. 4-toluenesulfonic acid, or a base, e.g. pyridine.

The compounds of the invention are generally characterized by the pharmacological activity hereinbefore stated, making them useful in counteracting certain physiological abnormalities in a living animal body. Effective quantities of the pharmacologically active compounds of the invention may be administered to a living animal body in anyone of various ways, for example orally as in capsules or tablets, parenterally in the form of sterile solutions, suspensions. and by pellet implantation. Among routes of parenteral administration are intravenously, subcutaneously, intramuscularly, intraperitoneally, intraarticularly, and intradermally. Other modes of administration are vaginally, rectally, and topically as e.g. in the form of ointments, suppositories, and powders.

As representative of living animal bodies, which may be treated with the compounds and compositions of the invention, and according to the method of treatment of the invention, for alleviation of the same and/or similar conditions as those described, in addition the following may be mentioned: domestic animals such as dogs and cats and farm animals such as horses, cows, sheep, and goats.

Pharmaceutical formulations are usually prepared from a predetermined quantity of one or more of the compounds of the invention. Such formulations may take the form of powder, syrups, suppositories, ointments, solutions, pills, capsules, pellets or tablets, suspensions, emulsions, oil solutions etc., with or without, but preferably with, any one of a large variety of pharmaceutically acceptable vehicles or carriers. When in a mixture with a pharmaceutical vehicle or carrier, the active ingredient usually comprises from about 0.01 to about 75 percent, normally from about 0.05 to about 15 percent, by weights of the composition. Carriers such as starch, sugar, talc, commonly used synthetic and natural gums, water, and the like, may be used in such formulations. Binders such as polyvinylpyrrolidone and lubricants such as sodium stearate, may be used to form tablets. Disintegrating agents such as sodium bicarbonate may also be included in tablets.

Although relatively small quantities of the active materials of the invention, even as low as 5.0 milligrams, may be used in cases of administration to subjects having a relatively low body weight, unit dosages are preferably five milligrams or above and preferably twenty-five, fifty, or one hundred milligrams, or even higher, depending of course upon the subject treated and the particular result desired, as will be apparent to one skilled in the art. Broader ranges appear to be 1 to 1000 milligrams per unit dose.

The active agents of the invention may be combined for administration with other pharmacologically active agents such as analgesics, steroids or hormones, or the like, or with buffers, antacids or the like, and the proportion of the active agent or agents in the compositions may be varied widely. It is only necessary that the active ingredient of the invention constitutes an effective amount, i.e. such that a suitable effective dosage will be obtained consistent with the dosage form employed. Obviously, several unit dosage forms may be administered at about the same time. The exact individual dosages as well as daily dosages in a particular case will of course be determined according to well established medical and/or veterinary principles under the supervision of the physician or veterinarian in charge. As a rule, however, when used therapeutically, the present compounds may be administered in a quantity of 1 to 1000 milligrams, preferred ranges being 1-100 milligrams per day and subject or patient, divided in 1 to 4 or more doses, over a suitable period and depending upon the subject and the type of subject being treated.

The following examples are intended to illustrate but not to limit the scope of the invention, although the compounds named are of particular interest for our intended purposes. These compounds have been designated by underlined numbers which are used in the biological examples below. The NMR data given in the examples are obtained from solutions in deuterated chloroform using a 60 MHz instrument (Perkin-Elmer R 12).

EXAMPLE 1

A mixture of 17α-hydroxypregn-4-ene-3,20-dione (20.0 g) and chloroacetic anhydride (145 g) is heated at 85° C. for 22 h. After cooling chloroform (200 ml) is added, and the solution is washed with H$_2$O and aq. NaHCO$_3$, dried, and evaporated to give an oil, to which ether (50 ml) is added. The precipitate is filtered off and the filtrate evaporated to dryness. The residue is dissolved in a mixture of conc. H$_2$SO$_4$ (2 ml), methanol (100 ml), and toluene (100 ml). After 3 h at 50° C., the solution is evaporated and the residue dissolved in chloroform (200 ml). After washing with aq. NaHCO$_3$ and H$_2$O, drying, and evaporation an oil is obtained, from which on treatment with ether (25 ml) crystals of 17α-chloroacetoxy-pregn-4-ene-3,20-dione (1, 13.1 g) deposit. M.P. 216°-7° C. after recrystallization from acetone/H$_2$O.

The structure is confirmed by NMR, IR, and analysis for Cl. The significant signals of the NMR spectrum are the following: δ (ppm) 0.70 (s, 3H, H-18), 1.20 (s, 3H, H-19), 2.09 (s, 3H, —COCH$_3$), 4.12 (s, 2H, —CH$_2$Cl), 5.80 (broad s, 1H, H-4).

In substantially the same manner the following compounds are obtained from the corresponding starting materials. The structures of the compounds are confirmed as above.

2. 17α-bromoacetoxypregn-4-ene-3,20-dione,
3. 17α-chloroacetoxy-6α-methylpregn-4-ene-3,20-dione,
4. 6-chloro-17α-(2-chloropropanoyloxy)pregna-4,6-diene-3,20-dione,
5. 17α-(2-bromopropanoyloxy)-6-methylpregna-4,6-diene-3,20-dione,
6. 17α-bromoacetoxy-6α-fluoropregn-4-ene-3,20-dione,
7. 6-chloro-17α-chloroacetoxy-16-methylenepregna-4,6-diene-3,20-dione,
8. 17α-bromoacetoxy-6-chloro-16α-methylpregna-4,6-diene-3,20-dione, and
9. 6-chloro-17α-chloroacetoxy-1α,2α-methylenepregna-4,6-diene-3,20-dione.

EXAMPLE 2

To a mixture of 4-bromobutyric acid (80.8 g) and trifluoroacetic anhydride (68.0 ml) 17α-hydroxypregn-4-ene-3,20-dione (80.0 g) is added. After 48 h at 4° C. the reaction mixture is poured into an ice-dichloromethane mixture. The organic phase is washed with H$_2$O and aq. NaHCO$_3$, dried, and evaporated to give an oil, which is dissolved in a mixture of conc. H$_2$SO$_4$ (4 ml), methanol (200 ml), and toluene (200 ml). After 3 h at 50° C. the solution is worked up as described in Example 1 to give 17α-(4-bromobutanoyloxy)pregn-4-ene-3,20-dione (1, 99.0 g) M.P. 134°-5° C. (acetone/H$_2$O).

The structure is confirmed by NMR, IR, and analysis for Br. The significant signals of the NMR spectrum are the following: δ (ppm) 0.70 (s, 3H, H-18), 1.20 (s, 3H, H-19), 2.06 (s, 3H, —COCH$_3$), 3.48 (t, 2H, —CH$_2$Br, J=6 Hz), 5.78 (broad s, 1H, H-4).

In substantially the same manner the following compounds are obtained from the corresponding starting materials. The structures of the compounds are confirmed as above.

2. 17α-(4-chlorobutanoyloxy)-19-norpregn-4-ene-3,20-dione,
3. 17α-(5-bromopentanoyloxy)-6α-fluoropregn-4-ene-3,20-dione,
4. 17α-(4-bromobutanoyloxy)-6α-methylpregn-4-ene-3,20-dione,
5. 17α-(4-bromobutanoyloxy)-6-chloropregna-4,6-diene-3,20-dione,
6. 17α-(4-bromobutanoyloxy)-6-methylpregna-4,6-diene-3,20-dione, and
7. 17α-(4-bromobutanoyloxy)-6-chloro-1α,2α-methylenepregna-4,6-diene-3,20-dione.

EXAMPLE 3

4-/N,N-bis(2-chloroethyl)amino/phenylacetic acid (22.1 g) is added to a solution of tetrabutylammonium hydrogen sulfate (27.2 g) in 2 M NaOH (80.0 ml). The mixture is vigorously stirred for 3 min and then extracted with chloroform (3×150 ml). To the dried extract 17α-chloroacetoxypregn-4-ene-3,20-dione (24.4 g), prepared according to Example 1, is added, and the mixture is refluxed for 16 h. The residue, obtained after evaporation of the solvent, is chromatographed on a silica gel column using toluene/ethyl acetate (2:1) as eluent. The eluate fraction having R$_f$=0.40 gives 17α-/4-(N,N-bis(2-chloroethyl)amino)phenylacetoxyacetoxy/pregn-4-ene-3,20-dione (1, 33.4 g), m.p. 72°-73° C. after recrystallization from methanol.

The structure is confirmed by NMR, IR, and analysis for Cl and N. The significant signals of the NMR spectrum are the following: δ (ppm) 0.70 (s, 3H, H-18), 1.20 (s, 3H, H-19), 2.05 (s, 3H, —COCH$_3$), 3.65 (s, 10H,22—CH$_2$CH$_2$Cl and —OCOCH$_2$ φ-), 4.63 (s, 2H, —OCOCH$_2$OCO—), 5.75 (broad s, 1H, H-4), 6.65 (d, 2H, aromatic H, J=8 Hz), 7.13 (d, 2H, aromatic H, J=8 Hz).

In substantially the same manner the following compounds are obtained from the corresponding haloesters of 17α-hydroxysteroids, prepared according to Examples 1 and 2, and the corresponding acids. The structures of the compounds are confirmed as above.

2. 17α-/4-(4-(N,N-bis(2-chloroethyl)amino)phenyl)butanoyloxyacetoxy/pregn-4-ene-3,20-dione,
3. 17α-/4-(4-(N,N-bis(2-chloroethyl)amino)phenyl)butanoyloxy)butanoyloxy/pregn-4-ene-3,20-dione,
4. 17α-/4-(4-(N,N-bis(2-chloroethyl)amino)phenylacetoxyy)butanoyloxy/pregn-4-ene-3,20-dione,
5. 17α-/4-(N,N-bis(2-chloroethyl)amino)phenylthioacetoxyacetoxy/pregn-4-ene-3,20-dione,
6. 17α-/3-(N,N-bis(2-chloroethyl)amino)benzoyloxyacetoxy/pregn-4-ene-3,20-dione,
7. 17α-/3-(N,N-bis(2-chloroethyl)amino)-4-methylbenzoyloxyacetoxy/pregn-4-ene-3,20-dione,
8. 6-chloro-17α-/2-(5-(4-(N,N-bis(2-chloroethyl)amino)phenyl)pentanoyloxy)propanoyloxy/pregna-4,6-diene-3,20-dione,
9. 17α-/2-((2E)-3-(2-(N,N-bis(2-chloroethyl)amino)phenyl)propenoyloxy)propanoyloxy/-6-methylpregna-4,6-diene-3,20-dione,
10. 17α-/5-(2-amino-3-(4-(N,N-bis(2-chloroethyl)amino)phenyl)propanoyloxy)pentanoyloxy/-6α-fluoropregn-4-ene-3,20-dione,
11. 6-chloro-17α-[4-(4-(N,N-bis(2-chloroethyl)amino)phenyl)butanoyloxyacetoxy]-1α,2α-methylenepregna-4,6-diene-3,20-dione,
12. 17-[(2S)-2-amino-3-(4-(N,N-bis(2-chloroethyl)amino)phenyl)propanoyloxyacetoxy]pregn-4-ene- 3,20-dione (prepared from the corresponding N-benzyl derivative)

12a. and its hydrochloride (12a, prepared by treatment of the free amine with HCl), 13. 17-[4-((2S)-2-amino-3-(4-(N,N-bis(2-chloroethyl)amino)phenyl)propanoyloxy)butanoyloxy]pregn-4-ene-3,20-dione (prepared from the corresponding N-carbonyloxybenzyl 13a. derivative) and its hydrochloride (13a, prepared by treatment of the free amine with HCl), 14. 17-[(2S)-2-acetamido-3-(4-(N,N-bis(2-chloroethyl)amino)phenyl)propanoyloxyacetoxy]pregn-4-ene-3,20-dione, 15. 17-[4-((2S)-2-acetamido-3-(4-(N,N-bis(2-chloroethyl)amino)phenyl)propanoyloxy)butanoyloxy]-pregn-4-ene-3,20-dione, 16. 17α-[4-(4-(N,N-bis(2-chloroethyl)amino)phenyl)-butanoyloxyacetoxy]-6α-methylpregn-4-ene-3,20-dione, 17. 17α-[4-(N,N-bis(2-chloroethyl)amino)phenylacetoxyacetoxy]-6-methylpregna-4,6-diene-3,20-dione, 18. 6-chloro-17α-[3-(N,N-bis(2-chloroethyl)amino)-4-methylbenzoyloxyacetoxy]pregna-4,6-diene-3,20-dione, 19. 17-[(2S)-2-amino-3-(3-(N,N-bis(2-chloroethyl)amino)phenyl)propanoyloxyacetoxy]pregn-4-ene-3,20-dione (prepared from the corresponding N-carbonyloxybenzyl 19a. derivative) and its hydrochloride (19a, prepared by treatment of the free amine with HCl), 20. 17-[(2S)-2-amino-3-(2-(N,N-bis(2-chloroethyl)amino)phenyl)propanoyloxyacetoxy]pregn-4-ene-3,20-dione (prepared from the corresponding N-carbonyloxybenzyl 20a. derivative) and its hydrochloride (20a, prepared by treatment of the free amine with HCl), 21. 17α-[4-(4-(4-(N,N-bis(2-chloroethyl)amino)phenyl)-butanoyloxy)butanoyloxy]-6α-methylpregn-4-ene-3,20-dione, 22. 6-chloro-17α-[4-(4-(N,N-bis(2-chloroethyl)amino)-phenylacetoxy)butanoyloxy]pregn-2,4-diene-3,20-dione, 23. 17α-[4-(3-(N,N-bis(2-chloroethyl)amino)-4-methyl-benzoyloxy)butanoyloxy]-6-methylpregna-4,6-diene-3,20-dione, 24. 6-chloro-17α-[4-(4-(4-(N,N-bis(2-chloroethyl)amino)phenyl)butanoyloxy)butanoyloxy]-1α,2α-methylenepregna-4,6-diene-3,20-dione, 25. 17α-[4-chloro-3-(N,N-bis(2-chloroethyl)amino)ben-zoyloxyacetoxy]-6α-fluoropregn-4-ene-3,20-dione, and 26. 17α-[3-(4-(N,N-bis(2-chloroethyl)amino)phenoxy)-propionyloxyacetoxy]pregn-4-ene-3,20-dione.

EXAMPLE 4

A mixture of 17α-chloroacetoxypregn-4-ene-3,20-dione (40.7 g), prepared according to Example 1, and NaN₃ (32.6 g) in 60% acetone (500 ml) is refluxed for 16 h. The acetone is removed by evaporation, and the aqueous solution is extracted with a 1:1 mixture of ether and ethyl acetate (3×100 ml). The combined extracts are washed with H₂O, dried, and evaporated to give an oil, from which, on treatment with ether, crystals of 17α-azidoacetoxypregn-4-ene-3,20-dione (32.0 g) deposit.

A solution of triphenylphosphine (25.2 g) in benzene (100 ml) is added dropwise to a solution of the above azide (32.0 g) in benzene (200 ml). After 4 h reflux the solution is cooled to room temperature, and HCl is bubbled through the solution until precipitation begins. Ether is added to complete the precipitation, and the crystals formed are collected. The product is dissolved in dichloromethane, and the solution, after washing with aq. NaHCO₃ and H₂O, drying, and evaporation, gives the 1-oxa-4-azacyclohex-3-en-6-one A (9.40 g), formed by a spontaneous intramolecular condensation of 17α-aminoacetoxypregn-4-ene-3,20-dione. The structure of compound A is verified by its NMR spectrum: δ (ppm) 0.97 (s, 3H, H-18), 1.19 (s, 3H, H-19), 2.27 (s, 3H, CH₃—C=N—), 4.14 and 4.48 (doublets, 1H each, AB system with J=22 Hz, —N—CH₂—CO—), 5.75 (broad s, 1H, H-4).

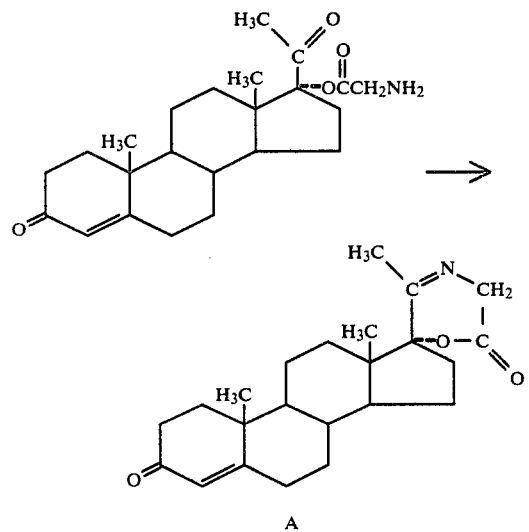

A

Compound A (9.40 g) is dissolved in a mixture of acetone (240 ml) and 0.15 M aq. KCl (120 ml). The pH is kept constant at 4.2 by a continuous addition of 5 M HCl. When the consumption of HCl has ceased, a solution of 4-/4-(N,N-bis(2-chloroethyl)amino)phenyl/-butanoic anhydride (22.0 g) in acetone (200 ml) is added and the pH is kept at 4.2 by a continuous addition of 5 M NaOH. When the consumption of NaOH has ceased the acetone is removed by evaporation, and the aqueous solution is extracted with ether/ethyl acetate (1:1, 3×100 ml). The extract is washed with 1 M aq. NaCO₃ and H₂O, dried, and evaporated. The residue is triturated in refluxing isopropyl ether and then recrystallized from ethyl acetate/isopropylether to give 17α-/4-(4-(N,N-bis(2-chloroethyl)amino)phenyl)-butanoylaminoacetoxy/pregn-4-ene-3,20-dione (1, 8.85 g, decomposes on heating).

The structure is confirmed by NMR, IR, and analysis for Cl and N. The significant signals of the NMR spectrum are the following: δ (ppm) 0.68 (s, 3H, H-18), 1.18 (s, 3H, H-19), 2.05 (s, 3H, —COCH₃), 3.65 (s, 8H, 2 —CH₂CH₂Cl), 4.03 (d, 2H, —COCH₂N<, J=6 Hz), 5.74 (broad s, 1H, H-4), 6.16 (t, 1H, >NH, J=6 Hz), 6.64 (d, 2H, aromatic H, J=7 Hz), 7.05 (d, 2H, aromatic H, J−7 Hz).

In substantially the same manner the following compound is obtained from the corresponding haloester of a 17α-hydroxysteroid, prepared according to Example 1, and the corresponding acid. The structure of the compound is confirmed as above.

2. 17α-/3-(N,N-bis(2-chloropropyl)amino)-4-methylbenzoylaminoacetoxy/-6α-methylpregn-4-ene-3,20-dione.

EXAMPLE 5

To a solution of tetrabutylammonium hydrogen sulfate (27.2 g) in 2 M NaOH (80.0 ml) 4-nitrobenzoic acid (13.4 g) is added. The mixture is vigorously stirred for 15 min and is then extracted with chloroform (3×150 ml). To the dried extract 17α-bromoacetoxypregn-4-ene-3,20-dione (27.2 g), prepared according to Example 1, is added. After 24 h reflux the solution is washed with $H_2O$, 2.5 M $H_2SO_4$, $H_2O$, aq. $NaHCO_3$, and $H_2O$, dried, and evaporated. On the addition of a 1:1 mixture of toluene/ethyl acetate (100 ml) to the residue crystals of 17α-(4-nitrobenzoyloxyacetoxy)pregn-4-ene-3,20-dione (29.1 g) precipitate.

The above 4-nitrobenzoic ester (29.1 g) is suspended in a mixture of tert. butanol (4300 ml) and $H_2O$ (700 ml), and 1 M KOH (58 ml) is added dropwise under stirring. After 16 h at room temperature $H_2O$ is added and the solution is extracted with chloroform (5×1000 ml). The combined extracts are dried and evaporated, and to the residue a 1:1 mixture of toluene/ethyl acetate (120 ml) is added. After 16 h at room temperature crystals of 17α-hydroxyacetoxypregn-4-ene-3,20-dione (11.0 g, m.p. 220°–1° C.) are filtered off. The compound exhibits the following significant NMR signals: δ (ppm) 0.70 (s, 3H, H-18), 1.19 (s, 3H, H-19), 2.06 (s, 3H, —COCH₃),

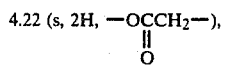

4.22 (s, 2H, —OCCH₂—), 5.31 (s, 1H, OH), 5.75 (broad s, 1H, H-4).

Additional 17α-hydroxyacetoxypregn-4-ene-3,20-dione (2.6 g) is obtained from the filtrate by chromatography on a silica gel column using toluene/ethyl acetate 1:2 as eluent ($R_f$=0.25).

The above alcohol is acetylated with acetic anhydride in pyridine to give 17α-acetoxyacetoxypregn-4-ene-3,20-dione, which shows the following significant NMR signals: δ(ppm) 0.69 (s, 3H, H-18), 1.19 (s, 3H, H-19), 2.07 and 2.17 (singlets, 3H each, 2-COCH₃),

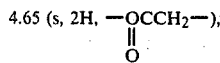

4.65 (s, 2H, —OCCH₂—), 5.76 (broad s, 1H, H-4).

A solution of the above alcohol (13.6 g) in abs. benzene (200 ml) is treated with phosgene at 5° C. After 16 h at room temperature the solution is evaporated to yield a crystalline residue, from which, on treatment with ether, 17α-chlorocarbonyloxyacetoxypregn-4-ene-3,20-dione (14.2 g) is obtained.

A solution of the above chloroformate (14. 2 g) in dry chloroform (100 ml) is added dropwise with stirring at 0° C. to a mixture of N,N-bis-(2-chloroethyl)-4-phenylenediamine hydrochloride (11.4 g) and triethylamine (7.95 g) in dry chloroform (100 ml). After 16h at room temperature the solution is washed with $H_2O$, 2 M HCl, and $H_2O$. Drying and evaporation give an oil, which is chromatographed on a silica gel column using toluene/ethyl acetate (2:1) as eluent. The fraction having a $R_f$-value of 0.28 yields 17α-/4-(N,N-bis(2-chloroethyl)amino)phenylcarbamoyloxyacetoxy/pregn-4-ene-3,20-dione (1, 7.35 m.p. 104°–5° C.).

The structure is confirmed by NMR, IR, and analysis for Cl and N. The significant signals of the NMR spectrum are the following: δ (ppm) 0.66 (s, 3H, H-18), 1.13 (s, 3H, H-19), 2.08 (s, 3H, —COCH₃), 3.66 (s, 8H, 2 —CH₂CH₂Cl), 4.68 (s, 2H, —OCOCH₂OCO—), 5.69 (broad s, 1H, H-4), 6.64 (d, 2H, aromatic H, J=9 Hz), 7.27 (d, 2H, aromatic H, J=9 Hz).

In substantially the same manner the following compounds are obtained from the corresponding haloesters of 17α-hydroxysteroids, prepared according to Example 1, and the corresponding 4-phenylenediamine and 4-aminophenol, respectively. The structures of the compounds are confirmed as above.

2. 6-chloro-17α-/4-(N,N-bis(2-chloroethyl)amino)-2-methoxyphenylcarbamoyloxyacetoxy/-16-methylenepregna-4,6-diene-3,20-dione,
3. 6-chloro-17α-/4-(N,N-bis(2-chloroethyl)amino)-phenoxycarbonyloxyacetoxy/-16α-methylpregna-4,6-diene-3,20-dione, and
4. 17α-[4-(N,N-bis(2-chloroethyl)amino)phenoxycarbonyloxyacetoxy]pregn-4-ene-3,20-dione.

EXAMPLE 6

To a solution of tetrabutylammonium hydrogen sulfate (17.0 g) in 5 M NaOH (10.0 ml) NaN₃ (3.25 g) is added. The solution is extracted with dichloromethane (100 ml), and to the dried extract toluene (100 ml) is added. The dichloromethane is removed by evaporation, and to the toluene solution 17α-(4-bromobutanoyloxy)pregn-4-ene-3,20-dione (17.2 g), prepared according to Example 2, is added. After 20 H at room temperature the solution is washed with $H_2O$, dried, and evaporated. The residue, on treatment with ether, yields 17α-(4-azidobutanoyloxy)pregn-4-ene-3,20-dione (14.2 g).

A mixture of trimethyl phosphite (5.8 g), the above azide (14.2 g), and toluene (130 ml) is heated at 85° C. for 3 h. The solution is evaporated, and to the residue methanol (250 ml) and 1 M HCl (250 ml) are added. After 3 h at 45° C. the methanol is evaporated, the aqueous solution is washed with ethyl acetate, and the aqueous phase is extracted with dichloromethane. After drying and evaporation of the extract 17α-(4-aminobutanoyloxy)pregn-4-ene-3,20-dione hydrochloride (29.1 g) is obtained.

The above amine hydrochloride is acetylated with acetyl chloride to give 17α-(4-acetylaminobutyanoyloxy)pregn-4-ene-3,20-dione, which shows the following significant NMR signals: δ (ppm) 0.65 (s, 3H, H-18), 1.19 (s, 3H, H-19), 2.00 and 2.10 (singlets, 3H each, 2-COCH₃), 5.70 (broad s, 1H, H-4), 7.42 (broad t, 1H, NH).

To a mixture of acetone (1200 ml) and 0.15 M KCl (400 ml) 4-/N,N-bis(2-chloroethyl)amino/phenylacetic anhydride (42.8 g) is added. pH of the solution is adjusted to 6.0, and a solution of the above amine hydrochloride (29.1 g) in a mixture of acetone (1200 ml) and 0.15 M KCl (400 ml) is added. The pH is maintained at 6.0–6.5 by a continuous addition of 5 M NaOH. When the comsumption of NaOH has ceased, the acetone is removed by evaporation and the aqueous solution extracted with ethyl acetate (2400 ml). The organic phase is washed with 1 M Na₂CO₃ and $H_2O$, dried, and evaporated to give 17α-/4-(4-(N,N-bis(2-chloroethyl)amino)-phenylacetylamino)butanoyloxy/pregn-4-ene-3,20-dione (1, 41.0 g, decomposes on heating).

The structure is confirmed by NMR, IR, and analysis for Cl and N. The significant signals of the NMR spectrum are the following: δ (ppm) 0.65 (s, 3H, H-18), 1.19 (s, 3H, H-19), 1.99 (s, 3H, —COCH₃), 3.37 (s, 2H, —COCH₂φ-), 3.69 (s, 8H, 2-CH₂CH₂Cl), 5.70 (broad s, 1H, H-4), 6.68 (d, 2H, aromatic H, J=9 Hz), 7.17 (d, 2H, aromatic H, J=9 Hz).

In substantially the same manner the following compounds are obtained from the corresponding haloesters of 17α-hydroxysteroids, prepared according to Example 2, and the corresponding acids. The structures of the compounds are confirmed as above.

2. 17α-/4-(2-(4-(N,N-bis(2-chloroethyl)amino)phenyl)-2-methylpropanoylamino)butyanoyloxy/-19-nor-pregn-4-ene-3,20-dione
3. 17α-/5-(3-(N,N-bis(2-bromoethyl)amino)-4-methylbenzoylamino)pentanoyloxy/-6α-fluoropregn-4-ene-3,20-dione, and
4. 17α-[4-(3-(N,N-bis(2-chloroethyl)amino-4-methylbenzoylamino)butanoyloxy]pregn-4-ene-3,20-dione.

EXAMPLE 7

A mixture of 3-/N,N-bis(2-chloroethyl)amino/-4-methylbenzoic acid (27.6 g) and trifluoroacetic anhydride (21.0 g) is heated under stirring at 60° C. for 15 min. To the mixture 17α-hydroxypregn-4-ene-3,20-dione (16.5 g) is added and the mixture is heated under stirring at 80° C. for 5 h. Toluene (150 ml) is added, the solution is filtered, and to the filtrate chloroform (200 ml) is added. After washing with H₂O and aq. NaHCO₃, drying, and evaporation an oil is obtained, to which a mixture of methanol (300 ml) and conc. HCl (3 ml) is added. After 16 h at room temperature the solution is evaporated and the residue chromatographed on a silica gel column using toluene/ethyl acetate (2:1) as eluent. The eluate fraction having $R_f=0.40$ gives 17α-/3-(N,N-bis(2-chloroethyl)amino)-4-methylbenzoyloxy/pregn-4-ene-3,20-dione (1, 6.8 g, m.p. 170°-1° C.).

The structure is confirmed by NMR, IR, and analysis for Cl and N. The significant signals of the NMR spectrum are the following: δ (ppm) 0.75 (s, 3H, H-18), 1.23 (s, 3H, H-19), 2.00 (s, 3H, —COCH₃), 2.40 (s, 3H, aromatic CH₃), 3.45 (s, 8H, 2-CH₂CH₂Cl), 5.76 (broad, s, 1H, H-4), 7.34 (d, 1H, aromatic H, J=8 Hz), 7.71 (dd, 1H, aromatic H, J¹=8 Hz and J²=2 Hz), 7.86 (d, 1H, aromatic H, J=2 Hz).

In substantially the same manner the following compounds are obtained from the corresponding starting materials. The structures of the compounds are confirmed as above.

2. 17α-/4-(N,N-bis(2-chloroethyl)amino)phenylacetoxy/pregn-4-ene-3,20-dione,
3. 17α-/4-(4-(N,N-bis(2-chloroethyl)amino)phenyl)butanoyloxy/pregn-4-ene-3,20-dione,
4. 17α-/4-(3-(N,N-bis(2-chloroethyl)amino)-4-methylbenzoyloxy)butanoyloxy/pregn-4-ene-3,20-dione, and

EXAMPLE 8

To a mixture of 1,2-dimethoxyethane (125 ml) and 70% HClO₄ (6.5 g) HgO (10.8 g) is added. The mixture is heated under stirring at 45°-55° C. for 25 min and is then cooled to room temperature. 17α-(4-bromobutanoyloxy)pregn-4-ene-3,20-dione (24.0 g), prepared according to Example 2, and H₂O (10 ml) are added, and the reaction mixture is stirred at room temperature for 5 h. Chloroform (100 ml) is added, the mixture is filtered, and the filtrate is washed with H₂O, aq. NaHCO₃, and H₂O. The residue, obtained after drying and evaporation, is chromatographed on a silica gel column using toluene/ethyl acetate (1:4) as eluent. 17α-(4-hydroxybutanoyloxy)pregn-4-ene-3,20-dione (13.6 g, m.p. 161°-2° C.) is obtained from an eluate fraction having $R_f=0.20$. The structure is confirmed by NMR and IR. The following NMR signals are significant: δ (ppm) 0.68 (s, 3H, H-18), 1.20 (s, 3H, H-19), 1.99 (s, 3H, —COCH₃), 4.19 (t, 1H, OH, disappears on addition of HCOOH), 5.70 (broad s, 1H, H-4).

The alcohol is acetylated with acetic anhydride in pyridine to give 17α-(4-acetoxybutanoyloxy)pregn-4-ene-3,20-dione, which exhibits the following significant NMR signals: δ (ppm) 0.69 (s, 3H, H-18), 1.19 (s, 3H, H-19), 2.02 and 2.06 (singlets, 3H each, 2-COCH₃),

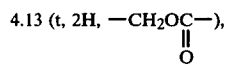

5.75 (broad s, 1H, H-4).

EXAMPLE 9

This example illustrates the effect of the compounds of the general formula I in inhibiting the growth of tumours.

LD50 is the dose that causes a 50 percent lethality of the animals, and ED50 is the dose that causes a 50 percent reduction of tumour size.

From the data below it is obvious that the compounds have a very low toxicity, and that the therapeutic indexes (T.I.), i.e. the ratios LD50/ED50, are very high.

The experimental design and the interpretation of the results are in accordance with the standards set by the CCNSC (Cancer Chemotherpy Reports, January 1959 and December 1962).

Some of the results obtained are given in the tables below. The compounds are named by number code, a:b, where a means the example, wherein the preparation of the compound in question is described, and b refers to the order of the compounds prepared according to that example. Thus, compound 4:2 means the second compound prepared according to Example 4. The systematic names of the compounds are given in the examples.

This example shows that the new compounds are useful to interfere with and suppress the growth of tumours and in some cases even cause complete remission of tumours and therefore can be employed in treating a living animal body suffering from disorders responsive to treatment with anticancer agents and with immunosuppressive agents.

Table 1.

Walker carcinosarcoma 256.

Experimental animals: Sprague-Dawley rats.
Tumour implant: Tumour pieces with 2-4 mm diameter, subcutaneously.
Therapy: Daily p.o. administration for 5 days starting on the day following implantation.
Termination: The animals are killed on the 9th day.
Evaluation: Weights of tumours of test animals are compared with those of control animals.
Results:

| Compound | LD50 | ED50 | T.I. |
|---|---|---|---|
| 3:1 | >250 | 8 | >31 |
| 3:2 | >250 | 3 | >83 |
| 3:3 | 40 | 2 | 20 |
| 3:4 | 80 | 4 | 20 |

Table 1.-continued

Walker carcinosarcoma 256.

Experimental animals: Sprague-Dawley rats.

Tumour implant: Tumour pieces with 2-4 mm diameter, subcutaneously.

Therapy: Daily p.o. administration for 5 days starting on the day following implantation.

Termination: The animals are killed on the 9th day.

Evaluation: Weights of tumours of test animals are compared with those of control animals.

Results:

| Compound | LD50 | ED50 | T.I. |
|---|---|---|---|
| 3:7 | >250 | 16 | >15 |

The following additional compounds exhibit antitumour activity in the foregoing test: 3:5, 3:6, 3:11, 3:12, 3:14, 3:16, 3:18, 3:21, 4:1, 5:1, 6:1, and 7:4.

Table 2.

Hepatome AH 130.

Experimental animals: Sprague-Dawley rats.

Tumour implant: $5 \times 10^6$ tumour cells i.p.

Therapy: One injection i.p. on the day following implantation.

Termination: The animals are killed on the 8th day.

Evaluation: Weights of tumours of test animals are compared with those of control animals.

Results:

| Compound | ED50 | T.I. |
|---|---|---|
| 3:1 | >250 | 3 | >83 |
| 3:2 | >1000 | 100 | >10 |
| 3:3 | 180 | 6 | 30 |
| 3:4 | 50 | 2 | 25 |
| 3:5 | >250 | 50 | >5 |
| 3:7 | >250 | 2 | >125 |
| 4:1 | >250 | 125 | >2 |
| 5:1 | >250 | 30 | >8 |
| 7:4 | >250 | 16 | >15 |

The following additional compounds exhibit antitumour activity in the foregoing test: 3:6, 3:8, 3:9, 3:10, 3:13, 3:15, 3:17, 3:19, 3:20, 3:22, 3:23, 3:24, 3:25, 3:26, 4:2, 5:2, 5:3, 5:4, 6:2, 6:3, and 6:4.

Table 3.

Ehrlich ascites tumour, ELD hyperdiploid (46 chromosomes).

Experimental animals: SPF NMRI mice.

Tumour implant: $2 \times 10^6$ tumour cells i.p.

Therapy: One injection i.p. on the day following implantation.

Termination: The animals are killed on the 8th day.

Evaluation: Weight of tumours of test animals compared with those of control animals.

Results:

| Compound | Dose (mg/kg) | Mortality | Tumour weight Treated/Control (%) |
|---|---|---|---|
| 3:1 | 50 | 1/12 | 3 |
| 3:2 | 50 | 0/12 | 1 |
| 3:7 | 100 | 0/12 | 2 |
| 5:1 | 1000 | 0/12 | 1 |

The following additional compounds exhibit antitumour activity in the foregoing test: 3:3, 3:4, 3:5, 3:6, 3:8, 3:9, 3:11, 3:12, 3:14, 3:16, 4:1, 5:1, 5:4, 6:1, 6:4, and 7:4.

Table 4.

Lymphatic leukemia L 1210.

Experimental animals: $CDF_1$ ($C3H \times DBA/2)F_1$ mice

Tumour implant: $10^5$ tumour cells i.p.

Therapy: One injection i.p. on the day following implantation.

Evaluation: (a) The survival time of the test animals (t) expressed as the percentage of that of control animals (c).

Effect (%) = $\frac{t \cdot 100}{c}$ (b) Weight change in the test animals (T) compared with that of the control animals (C) up to the 5th day.
$\Delta_v = T - C$ (c) The mortality rate must not exceed 35% in the test animals on the 5th day of therapy.

Results:

| Compound | Dose (mg/kg) | Mortality | Weight change $\Delta_v(g)$ | Effect (%) |
|---|---|---|---|---|
| 3:7 | 500 | 0/19 | −5.2 | 172 |
| 3:7 | 250 | 0/20 | −4.0 | 130 |

EXAMPLE 10

This example illustrates the compound's relative affinity to rabbit uterus cytosol progesterone receptor compared with progesterone. The method used for this purpose is a modification of methods already described by Kontula, K. et al. (Acta Endocrinol. 78 (1975) 574) and Terenius, L. (Steroids 23 (1974) 909) among others.

Cytosol preparation

Female rabbits (3-4 pounds) from Knut Larsen, Uddevalla, Sweden, were injected i.m. with 1 mg Estradurin (polyestradiol phosphate, 1 mg/ml saline, AB Leo, Sweden). After one week, the animals were killed and the uteri were immediately removed, chilled and cut free from connective tissues. All the following operations were performed at 0°-4° C. The uteri were cut into small pieces and washed several times with 3 vol. of buffer at pH 7.4 containing 50 MM TRIS-HCl, 1.5 mM EDTA, 3 mM $NaN_3$, 2 mM dithiothreitol, and 25% glycerol (by vol.). The tissue was homogenized in the same buffer (3 vol.) with four 15-s bursts at rheostat setting 36-37 of an Ultra Turrax (Janke and Kunkel KG, Staufen, The Federal Republic of Germany). The homogenate was centifuged in a Sorvall GLC-2 centrifuge for 15 min at $600 \times g$. The supernatanate was recentrifuged at $105,000 \times g$ for 60 min in a Beckman ultracentrifuge model LB-65-B with rotor SW 56.

One ml portions of the supernatant (rabbit uterus cytosol) were pipetted into small centrifuge tubes of glass and were kept at −70° C. until used. The protein content was determined by the method of Lowry (J. Biol. Chem. 193 (1951) 265).

Dissolving the compounds 10.0 mg of each compound was dissolved in 10.0 ml 99.5% ethanol. 100 μl of this standard solution was diluted to 5.0 ml ethanol/glycerol 1:1 (v/v). The ethanol was evaporated by blowing air at 40° C. on the solution. The volume was then adjusted to 5.0 ml by adding buffer without glycerol.

Incubation of the compounds

The compounds were diluted with glycerol/buffer 1:1 to final concentrations between $10^{-8}$–$10^{-5}$ M in total 300 μl incubation media. 100 μl of each compound and of each dilution were incubated in small centrifuge tubes (2 ml) together with 100 μl (10 pg) $^3$H-progesterone (1,2,6,7-3H-progesterone, 47.8 Ci/mMol, The Radiochemical Centre, Amersham, England) and 100 μl cytosol adjusted with buffer to a final concentration of about 0.7 g/ml. The incubations were carried out for 16–18 hours at 4° C.

The separation of bound from free radioactivity was carried out at 0° C. using the dextran coated charcoal technique (DCC). To each incubation tube was added 0.5 ml DCC-suspension (0.05% dextran-70, Pharmacia, Uppsala, Sweden and 0.5% Norit A, Sigma, Saint Louis, Missouri, U.S.A.) The tubes were agitated 2–3 times during 10 minutes whereupon they were centrifuged at 100×g for five minutes. The supernatantes were decanted directly into Scintillation vials (polyethene, Packard) containing 10 ml InstaGel (Packard). The radioactivity was counted in a Philip's liquid scintillation spectrometer Model PW 4510/00 with external standard and automatic quenching correction.

Standard curve for progesterone

To incubation tubes were added 100 µl cytosol, 100 µl $^3$H-progesterone (10 pg) and 100 µl of different dilutions of non-radioactive progesterone in glycerol/buffer 1:1 ranging from 0–10$^4$ pg/100 µl. The tubes were incubated parallel with the compounds described above. The radioactivity was calculated by substracting the counted radioactivity in the incubation tubes with the radioactivity counted in incubations tubes in which the cytosol was replaced with buffer (100 µl).

Calculations

The concentration of non-radioactive progesterone $[P]_i$ which competes for 50% of bound radioactive progesterone was calculated from the standard curve constructed $[B]_i/[B]_o = 0.5$ where $[B]_i$ is the bound radioactivity at different concentrations of non-radioactive progesterone and $[B]_o$ is the bound radioactivity at progesterone concentration zero.

In the same manner, curves were constructed for each compound X and the concentration for each compound which competes for 50% with bound $^3$H-progesterone ($[X]_{50}$) was calculated.

The relative binding affinity (RBA) in percent for each substance compared to progesterone was calculated and is summarized in the table below.

Table

| Compound | RBA |
|---|---|
| 3:3 | 0.6 |
| 3:2 | 0.7 |
| 7:4 | 0.9 |
| 4:1 | 1.1 |
| 3:7 | 1.8 |
| 3:1 | 6.6 |
| 5:1 | 15.8 |

From this example it is evident that the compounds have the ability to specifically concentrate in tumour cells rich in progesterone receptors, frequently found in mammary and endometrical tumours.

EXAMPLE 11

Manufacturing Process for tablets à 10 mg
Model batch of 1000 tablets.

| | | | |
|---|---|---|---|
| I | Compound 3:7, mesh* 70 | 10.0 | g |
| | Lactosum, Ph. Nord. | 210 | g |
| | Amylum maidis, Ph. Nord. | 75 | g |
| II | Kollidon 25, B.A.S.F. | 3.5 | g |
| | Aqua purificata q.s. | | |
| III | Talcum, Ph. Nord. | 15 | g |

_continued_

Manufacturing Process for tablets à 10 mg
Model batch of 1000 tablets.

| | | |
|---|---|---|
| Magnesii stearas, Ph. Nord. | 1.5 | g |
| Weight of 1000 tablets: | 315 | g |
| Weight of 1 tablet: 315 mg | | |

*The mesh standard is according to the international system of code DIN 4189/1968.
Punch: 10.5 mm round, flat, scored, bevel-edged.

Mix the screened substances I thoroughly and then moisten with II, whereupon it is granulated through a stainless sieve No. 10 (mesh 25). Dry the granulate in an oven at a maximum temperature of 40° C., then repeat sieving through sieve No. 10.

Add the substances under III and mix thoroughly. Punch tablets with a gross weight of about 315 mg.

EXAMPLE 12

| Injectable solution 10 mg/ml | |
|---|---|
| Compound 3:2, mesh 70 | 10 mg |
| Benzyl alcohol | 80 mg |
| Peanut oil to make | 1 ml |

The substance is dissolved in the benzyl alcohol and peanut oil is added.

EXAMPLE 13

| Vagitoria à 25 mg | |
|---|---|
| Compound 4:1 | 25 mg |
| Cacao butter | q.s. |

EXAMPLE 14

| Ointment 2% | | |
|---|---|---|
| Compound 5:1 | 2 | g |
| Triethanolamine | 1 | g |
| Glycerol | 7 | g |
| Cetanol | 2.5 | g |
| Lanoline | 2.5 | g |
| Stearic acid | 20 | g |
| Sorbitan monooleate | 0.5 | g |
| Sodium hydroxide | 0.2 | g |
| Methyl paraben | 0.3 | g |
| Propyl paraben | 0.1 | g |
| Ethanol | 0.9 | g |
| Water to make | 100 | g |

EXAMPLE 14a

Similar to Example 14 above, but compound 5:1 replaced by compound 7:4

EXAMPLE 15

| Capsules à 10 mg | |
|---|---|
| Compound 3:2 | 10 mg |
| Magnesium stearate | 2 mg |
| Talcum | 188 mg |

The substances are mixed and filled in capsules.

EXAMPLE 16

| Injectable solution 15 mg/ml | |
|---|---|
| Compound 3:3 | 15 mg |
| Benzyl benzoate | 120 mg |
| Castor oil to make | 1 ml |

The compound is dissolved in the benzyl benzoate and castor oil is added.

In the above Examples 11-16 to compositions the compounds are named according to the number code defined in Example 9. The Examples 11-16 are merely representative with regard to active ingredients exemplified. It is to be understood that other compounds disclosed in the foregoing Examples 3-7 may also be substituted for the active ingredients illustrated in the above examples.

Also, it is to be noted that two or more compounds of the invention may be used in combination in the compositions illustrated, and also, if desired, in combination with other pharmacologically active agents.

Various modifications and equivalents will be apparent to one skilled in the art and may be made in the compounds, compositions and methods of the present invention without departing from the spirit or scope thereof, and it is therefore to be understood that the invention is not to be limited to the specific examples and embodiments disclosed herein.

REFERENCES

1. Solo, A. J. and Gardner, J. O., J. Pharm. Sci. 60 (1971) 1089.
2. Huang-Minlon, Wilson, E., Wendler, N. L., and Tishler, M. J.A.C.S. 74 (1952) 5394.
3. Sandler, S. R. and Karo, W. Organic Functional Group Preparations. Academic Press, New York 1971, chapter 2.
4. Vitali, R., Gardi, R., and Ercoli, A. Gazz. Chim. Ital. 96 (1966) 1115.
5. McOmie, J. F. W. Protective Groups in Organic Chemistry. Plenum Press, London 1973.
6. Djerassi, C. Steroid Reactions. Holden-Day, San Francisco 1963, chapter 1.
7. Brändström, A. Preparative Ion Pair Extraction. Apotekarsocieteten/Hässle Läkemedel, Sweden 1974, p. 109.
8. Referenc 3, p. 252.
9. Reference 3, p. 247.
10. McKillop, A. and Ford, M. E. Tetrahedron 30 (1974) 2467.
11. Reference 3, p. 274.
12. Boyer, J. H. and Hamer, J. J. Amer. Chem. Soc. 77 (1955) 951.
13. Schoberl, A. and Wagner, A. in Muller, E. (Ed.) Methoden der organischen Chemie (Houben-Weyl) vol. 9 (1955) 749.
14. Reynolds, D. D. J. Org. Chem. 27 (1962) 93.
15. Reference 5, chapter 5.
16. McKillop, A., Fiaud, J.-C., and Hug, R. P. Tetrahedron 30 (1974) 1379.
17. Buehler, C. A. and Pearson, D. E. Survey of Organic Synthesis. Wiley, New York 1970, p. 287.
18. Cordes, E. H. in Patai, S. (Ed.). The Chemistry of Carboxylic Acids and Esters. Wiley, London 1969, chapter 13.
19. Sulzbacher, M., Bergmann, E. D., and Pariser, E. R. J. Amer. Chem. Soc. 70 (1948) 2827.
20. Rosenkranz, G. J., Pataki, J., and Djerassi, C. J. Org. Chem. 17 (1952) 290.
21. Fieser, L. F. J. Amer. Chem. Soc. 76 (1954) 1945.
22. Mazur, R. H. and Brown, E. A. J. Amer. Chem. Soc. 77 (1955) 6670.
23. Corey, E. J. and Mitra, R. B. J. Amer. Chem. Soc. 84 (1962) 2938.
24. Wunsch, E. in Muller E. (Ed.). Methoden der organischen Chemie (Houben-Weyl). Band XV/1, p. 47.
25. Levin, Y., Berger, A., and Katchalski, E. Biochem. J. 63 (1956) 308.
26. Baer, E., Maurukas, J., and Russell, M. J. Amer. Chem. Soc. 74 (1952) 152.
27. Haas, H. J. Chem. Ber. 94 (1961) 2442.
28. Buehler, C. A. and Pearson, D. E. Survey of Organic Syntheses. Wiley, New York 1970, p. 814.

We claim:

1. Novel compounds having the general formula $$St-R$$

wherein R is

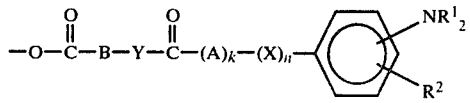

where $R^1$ is a β- or γ-halogensubstituted alkyl group having 2 to 4 carbon atoms, the halogen being chlorine or bromine;

where $R^2$ is selected from the group consisting of hydrogen, lower alkyl, lower alkoxy, and halogen;

where A is a straight hydrocarbon chain having at most 4 carbon atoms and being saturated or containing one double bond, at most 2 hydrogen atoms of A being replaced by lower alkyl and at most one of the hydrogen atoms situated at the carbon atom adjacent to a

group being replaced by a group selected from the group consisting of amino and lower alkanoylamino;

where B is a straight saturated hydrocarbon chain having at most 4 carbon atoms, at most 2 hydrogen atoms of B being replaced by lower alkyl;

where X and Y are independently selected from the group consisting of —O—, —NH, and —S—;

where k and n are independently selected from the group consisting of zero and one, n always being zero when k is zero; and where St is the radical of a steroid having a cyclopentanophenanthrene carbon-carbon skeleton containing up to a maximum of 40 carbon atoms, inclusive of substituents, said carbon-carbon skeleton having a steroid nucleus selected from the group consisting of pregnane and 19-norpregnane nuclei, having up to a maximum of two double bonds, said steroid radical being attached at its 17-position to R, said position being identified according to steroid nomenclature, wherein said steroid radical St, has a nucleus selected from the group consisting of: pregn-4-ene-3,20-dione, pregna-4,6-diene-3,20-dione, and 19-norpregn-4-ene-3,20-dione nuclei; and wherein any further substitution present in the carbon-carbon skeleton of said steroid nucleus of said steroid radical is at most a tetrasubstitution, where the positions of the steroid carbon-carbon skeleton which are substituted are selected from the positions consisting of 1-, 2-, 6-, and 16-positions, where the substitution, if any, comprises at least one substituent selected from the group consisting of methyl, methylene, fluoro, and chloro.

2. A compound according to claim 1, wherein said steroid radical, St, is selected from the group consisting of: 17-hydroxypregn-4-ene-3,20-dione, 17-hydroxy-6α-methylpregn-4-ene-3,20-dione, 6-chloro-17-hydroxypregna-4,6-diene-3,20-dione, 17-hydroxy-6-methylpregna-4,6-diene-3,20-dione, and 6-chloro-17-hydroxy-16α-methylpregna-4,6-diene-3,20-dione radicals.

3. A compound according to claim 2, wherein $R^1$ is a β-halogen substituted alkyl group, selected from the group consisting of β-halogen substituted ethyl, n-propyl, and n-butyl; wherein $R^2$ is hydrogen or lower alkyl; wherein the group —$NR^1_2$ is in m— or p-position when k and n are zero and in p-position when at least one of k and n is one; wherein $R^2$, when the group —$NR^1_2$ is in m-position, is in p-position; wherein, when A is substituted with an amino or a lower alkanoylamino group, n is zero and A is a saturated hydrocarbon chain containing two carbon atoms; wherein X, when present, is —O— or —NH—; and wherein Y, when present, is —O— or —NH—.

4. A compound according to claim 3, wherein $R^1$ is β-chloroethyl.

5. A compound according to claim 3, wherein n is zero.

6. A compound according to claim 1 selected from the group consisting of
17α-/2-((2E)-3-(2-(N,N-bis(2-chloroethyl)amino)-phenyl)-propenoyloxy)pronanoyloxy/-6-methyl-pregna-4,6-diene-3,20-dione, 6-chloro-17α-[4-(4-(N,N-bis(2-chloroethyl)amino)phenyl)butanoyloxyacetoxy]-1α,2α-methylenepregna-4,6-diene-3,20-dione,
17α-/5-(3-(N,N-bis(2-bromoethyl)amino)-4-methylben(s)zoylamino)pentanoyloxy/-6α-fluoropregn-4-ene-3,20-dione,
6-chloro-17-[4-(N,N-bis(2-chloroethyl)amino)-2-methoxyphenylcarbamoyloxyacetoxy]-16-methylenepregna-4,6-diene-3,20-dione, and
17-[4-(2-(4-(N,N-bis(2-chloroethyl)amino)phenyl)-2-methylpropanoylamino)butanoyloxy]-19-norpregn-4-ene-3,20-dione.

7. A compound according to claim 3, which is 17-[3-(N,N-bis(2-chloropropyl)amino)-4-methylbenzoylaminoacetoxy]-6α-methylpregn-4-ene-3,20-dione.

8. A compound according to claim 3, selected from the group consisting of
17-[4-(N,N-bis(2-chloroethyl)amino)phenylthioacetoxyacetoxy]pregn-4-ene-3,20-dione and
17-[3-(4-(N,N-bis(2-chloroethyl)amino)pheoxy)propionyloxyacetoxy]pregn-4-ene-3,20-dione.

9. A compound according to claim 3, selected from the group consisting of
17-[4-(N,N-bis(2-chloroethyl)amino)phenylcarbamoyloxyacetoxy]pregn-4-ene-3,20-dione, and
17-[4-(N,N-bis(2-chloroethyl)amino)phenoxycarbonyloxyacetoxy]pregn-4-ene-3,20-dione.

10. A compound according to claim 5, selected from the group consisting of
17-/3-(N,N-bis(2-chloroethyl)amino)benzoyloxyacetoxy/pregn-4-ene-3,20-dione,
17-/3-(N,N-bis(2-chloroethyl)amino)-4-methylbenzoyloxyacetoxy/pregn-4-ene/3,20-dione,
6-chloro-17-[3-(N,N-bis(2-chloroethyl)amino)-4-methylbenzoyloxyacetoxy]pregna-4,6-diene-3,20-dione, and
17-[4-(3-N,N-bis(2-chloroethyl)amino)-4-methylbenzoyloxy)butanoyloxy]pregn-4-ene-3,20-dione.

11. A compound according to claim 5, which is 17-[4-(3-N,N-bis(2-chloroethyl)amino)-4-methylbenzoylamino)butanoyloxy]pregn-4-ene-3,20-dione.

12. A compound according to claim 5, selected from the group consisting of
17-[4-(N,N-bis(2-chloroethyl)amino)phenylacetoxyacetoxy]pregn-4-ene-3,20-dione,
17-/4-(4-(N,N-bis(2-chloroethyl)amino)phenyl)-butanoyloxyacetoxy/pregn-4-ene-3,20-dione,
17-/4-(4-(4-(N,N-bis(2-chloroethyl)amino)phenyl)-butanoyloxy)butanoyloxy/pregn-4-ene-3,20-dione,
17-/4-(4-(N,N-bis(2-chloroethyl)amino)-phenylacetoxy)butanoyloxy/pregn-4-ene-3,20-dione,
17-[((2S)-2-amino-3-(4-(N,N-bis(2-chloroethyl)amino)phenyl)propanoyloxy)acetoxy]-pregn-4-ene-3,20-dione, and its hydrochloride,
17-[4-((2S)-2-amino-3-(4-(N,N-bis(2-chloroethyl)amino)phenyl)propanoyloxy)butanoyloxy]pregn-4-ene-3,20-dione, and its hydrochloride,
17-[((2S)-2-acetamido-3-(4-(N,N-bis(2-chloroethyl)amino)phenyl)propanoyloxy)acetoxy]pregn-4-ene-3,20-dione,
17-[4-(4-(N,N-bis(2-chloroethyl)amino)phenyl)-butanoyloxyacetoxy]-6α-methylpregn-4-ene-3,20-dione, and
17-[4-(N,N-bis(2-chloroethyl)amino)phenylacetoxyacetoxy]-6-methylpregna-4,6-diene-3,20-dione.

13. A compound according to claim 5, selected from the group consisting of
17-[4-(4-(N,N-bis(2-chloroethyl)amino)phenyl)-butanoylaminoacetoxy]pregn-4-ene-3,20-dione, and
17-[4-(4-(N,N-bis(2-chloroethyl)amino)-phenylacetylamino)butanoyloxy]pregn-4-ene-3,20-dione.

14. A pharmaceutical composition, comprising about 0.01 to about 75 weight percent of a compound of claim 1 and a pharmaceutical carrier.

15. A method for palliative treatment of tumors in a living animal which comprises administering to said animal an amount of a compound of claim 1 which is effective for said purpose.

16. Composition of claim 14, wherein the compound is a compound of claim 5.

17. Method of claim 15, wherein the compound is a compound of claim 5.

18. Composition of claim 14, wherein the compound is present in an amount of about 0.05 to about 15 percent by weight.

* * * * *

UNITED STATES PATENT AND TRADEMARK OFFICE
CERTIFICATE OF CORRECTION

PATENT NO. : 4,177,269

DATED : December 4, 1979

Page 1 of 2

INVENTOR(S) : Hans Fex, Bertil Hansen, Krister Holmberg, Bertil Högberg and Imre Könyves It is certified that error appears in the above—identified patent and that said Letters Patent is hereby corrected as shown below:

Col. 3, lines 57 and 61; "—$NR_2^1$" should read -- —$NR^1_2$ --
Col. 5, lines 18, 34 and 55; "$NR^1_2$" should read -- $NR^1_2$ --
Col. 7, line 60; " as tetrabutylammonium " should read -- as a tetrabutylammonium --
Col. 9, line 29; "amine" should read -- imine --
Col. 11, line 68; "suspensions." should read -- suspensions, --
Col. 14, lines 56, 62 and 68; ")" should read with the close parenthesis mark on the line it is enclosing and not standing alone. No dashes are necessary except after the ")".
Col. 15, lines 6, 12, 26, 32 and 47; ")" should read with the close parenthesis mark on the line it is enclosing and not standing alone. No dashes are necessary except after the ")".
Col. 16, line 63; "J-7" should read -- J=7 -- (second occurrence)
Col. 18, line 31; "20 H" should read -- 20 h --
Col. 18, lines 47 & 48; "(4-acetylaminobutyanoyloxy)" should read -- (4-acetylaminobutanoyloxy) --
Col. 19, line 12; "butyanoyloxy/" should read -- butanoyloxy/ --
Col. 19, lines 54 & 55; "-dione, and" should read with a period (.) after "-dione" and the "and" should be deleted.
Col. 22, line 38; "MM" should read -- mM --
Col. 25, under "REFERENCES", Ref. No. 8; "Referenc 3" should read -- Reference 3 --

UNITED STATES PATENT AND TRADEMARK OFFICE
CERTIFICATE OF CORRECTION

PATENT NO. : 4,177,269

DATED : December 4, 1979

INVENTOR(S) : Hans Fex, Bertil Hansen, Krister Holmberg, Bertil Höberg and Imre Könyves It is certified that error appears in the above—identified patent and that said Letters Patent is hereby corrected as shown below:

Col. 25, under "REFERENCES", Ref. No. 13; "Schoberl" should read -- Schöberl --
Col. 25, under "REFERENCES", Ref. No. 13; "Muller" should read -- Müller --
Col. 25, under "REFERENCES", Ref. No. 17; "Synthesis" should read
    -- Syntheses --
Col. 26, under "REFERENCES", Ref. No. 24; "Wunsch" should read -- Wünsch --
Col. 26, under "REFERENCES", Ref. No. 24; "Muller" should read -- Müller --
Col. 28, lines 33, 36 and 39; ")" should read with the close parenthesis
    mark on the line it is enclosing and not standing alone. No dashes
    are necessary except after the ")".
Col. 28, line 62 (Claim 16, line 2); "5" should read -- 2 --

Col. 28, line 64 (Claim 17, line 2); "5" should read -- 2 --
Column 27, line 67; "pheoxy should read -- phenoxy --

Signed and Sealed this

Nineteenth Day of August 1980

[SEAL]

Attest:

SIDNEY A. DIAMOND

Attesting Officer

Commissioner of Patents and Trademark